(12) United States Patent
Kimble et al.

(10) Patent No.: US 8,557,271 B2
(45) Date of Patent: Oct. 15, 2013

(54) DRUG DEPOT IMPLANTABLE WITHIN A JOINT

(75) Inventors: Toya D. Kimble, Memphis, TN (US); Susan J. Drapeau, Memphis, TN (US); William F. McKay, Memphis, TN (US); John Myers Zanella, Memphis, TN (US); Erica Tenbroek, Minneapolis, MN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 944 days.

(21) Appl. No.: 12/174,007

(22) Filed: Jul. 16, 2008

(65) Prior Publication Data

US 2010/0015196 A1 Jan. 21, 2010

(51) Int. Cl.
*A61K 9/24* (2006.01)
*A61P 29/00* (2006.01)
*A61P 25/00* (2006.01)

(52) U.S. Cl.
USPC ........................................... 424/423

(58) Field of Classification Search
None
See application file for complete search history.

(56) References Cited

U.S. PATENT DOCUMENTS

| | | | |
|---|---|---|---|
| 4,624,255 A | 11/1986 | Scheneck et al. | |
| 4,863,457 A | 9/1989 | Lee | |
| 5,522,844 A | 6/1996 | Johnson | |
| 5,868,789 A | 2/1999 | Huebner | |
| 6,756,058 B2 | 6/2004 | Brubaker et al. | |
| 6,960,215 B2 * | 11/2005 | Olson et al. ............... | 606/92 |
| 6,974,462 B2 | 12/2005 | Sater | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |
| 7,235,043 B2 | 6/2007 | Gellman et al. | |
| 7,318,840 B2 | 1/2008 | McKay | |
| 7,329,259 B2 | 2/2008 | Cragg | |
| 7,361,168 B2 | 4/2008 | Makower et al. | |
| 7,367,978 B2 | 5/2008 | Drewry et al. | |
| 7,741,273 B2 * | 6/2010 | McKay ........................ | 514/2 |
| 2005/0245905 A1 | 11/2005 | Schmidt et al. | |
| 2006/0085075 A1 * | 4/2006 | McLeer ................ | 623/17.12 |
| 2006/0106361 A1 | 5/2006 | Muni et al. | |
| 2006/0188546 A1 * | 8/2006 | Giroux ..................... | 424/426 |
| 2006/0259119 A1 | 11/2006 | Rucker | |
| 2007/0031472 A1 | 2/2007 | Huang et al. | |
| 2007/0053963 A1 * | 3/2007 | Hotchkiss et al. ........... | 424/448 |
| 2007/0185497 A1 | 8/2007 | Cauthen et al. | |
| 2007/0243225 A1 | 10/2007 | McKay | |
| 2007/0243228 A1 | 10/2007 | McKay | |
| 2008/0097606 A1 * | 4/2008 | Cragg et al. ............ | 623/14.12 |
| 2010/0076481 A1 * | 3/2010 | Stephens et al. ........... | 606/192 |

FOREIGN PATENT DOCUMENTS

| | | |
|---|---|---|
| WO | 0007521 A1 | 2/2000 |
| WO | 2007121288 A2 | 10/2007 |

OTHER PUBLICATIONS

Seo, S.-A. et al., "A local delivery system for fentanyl based on biodegradable poly(L-lactide-co-glycolide) oligomer". Int. J. Pharm., 2002, vol. 239, pp. 93-101. See abstract; table 1; figures 2-5; conclusion.
International Search Report and Written Opinion for International Application No. PCT/US2009/050520 mailed on Mar. 2, 2010.

* cited by examiner

*Primary Examiner* — Suzanne Ziska
(74) *Attorney, Agent, or Firm* — Sorell Lenna & Schmidt LLP

(57) ABSTRACT

Methods and compositions for treating a tissue within a synovial joint in a patient in need of such treatment are provided. The methods and compositions involve inserting a drug depot through the synovial joint and attaching the drug depot to the inside of the synovial joint capsule so that the drug depot does not substantially interfere with movement of the joint, wherein said depot comprises a polymer and at least one pharmaceutical agent.

20 Claims, 11 Drawing Sheets

DRUG DEPOT IMPLANTABLE WITHIN A JOINT

FIELD

A pharmaceutical depot is provided that can be used to treat diseases within a joint capsule. More particularly, the depot has a shape and characteristics, which permits unfettered movement of the bones, tendons and ligaments within the joint capsule while treating the disease over a period of time. Therapeutic modalities are disclosed for treating the diseased joint.

BACKGROUND

Synovial joints, such as the knee, are joints of the body where two adjacent bones are coupled and encapsulated within a synovial membrane or capsule. Ligaments connect bones together while tendons connect bone to muscle. Some joints have cartilage between two or more bones. A synovial membrane substantially surrounds the joint and encapsulates the synovial fluid that fills the joint, thereby forming the joint capsule. The synovial fluid functions to both lubricate and nourish the joint. A synovial joint functions to facilitate full range of normal articulation and movement of the joint that is unique to each patient. As such, maintaining the integrity of the joint allows performance of the patient's day-to-day activities.

There are numerous traumas and/or acute or chronic disorders, which affect the normal workings of a synovial joint and require therapeutic intervention. Examples of joint disorders include, but are not limited to, osteoarthritis, chondromalacia and rheumatoid arthritis, carpal tunnel syndrome, tarsal tunnel syndrome or the like. Additionally, the joint could simply be infected from a post-surgical or prior joint injury. In each of these disorders and traumas the joint is mechanically compromised, either acutely or chronically, causing the body to elicit an immune response. Such a response typically manifests itself as inflammation and/or persistent pain in the joint area.

An example of a joint is a knee joint which contains the tibia and the fibula extending up from the lower leg, the femur extending down from the thigh and the patella as the knee cap over the joint. The medial collateral ligament and the lateral collateral ligament connect the femur to the tibia and fibula, respectively, and restrict the sideways motion of the joint. The posterior cruciate ligament connects the femur to the tibia and restricts backward movement of the joint away from the patella. The anterior cruciate ligament connects the femur to the tibia and restricts the joint rotation and forward motion toward the patella. Examples of traumas to the knee joint include, but are not limited to, tearing and/or fracturing of the anterior cruciate ligament, posterior cruciate ligament, the medial collateral ligament, the lateral collateral ligament, the patellar ligament, the medial meniscus, the lateral meniscus and chondrol fractures.

Inflammation can be an acute response to trauma or a chronic response to the presence of inflammatory agents brought about by any number of processes or events which trigger tissue damage within the synovial joint. For example, when tissues are damaged, tumor necrosis factor-alpha (hereinafter "TNF-α") attaches to cells causing them to release other cytokines leading to an increase in inflammation. One type of recruited immune system cell is the macrophage. Macrophages release interleukin-1 beta ("IL-1β") and tumor necrosis factor-alpha ("TNF-α"), pro-inflammatory cytokines heavily involved in orchestrating the immediate and local physiological effects of injury or infection. For instance, once released, pro-inflammatory cytokines promote inflammation. The purpose of the inflammatory cascade is to promote healing of the damaged tissue. However, once the tissue is healed, the inflammatory process does not necessarily end. Left unchecked, the inflammatory process can lead to degradation of surrounding tissues and associated chronic pain. Thus, pain can become a disease state in itself. That is, when this pathway is activated, inflammation and pain ensue. Cycles of inflammation and associated pain often occur long after the initial trauma has or should have resolved.

Current treatment methods of inflammation of the joints include the use of pharmaceutical agents, which are designed to reduce inflammation such that the pain associated with the inflammation subsides and the subject regains at least partial use of the joint. Such pharmaceutical agents include, but are not limited to, analgesics and anti-inflammatory drugs. These drugs can be administered systemically and/or injected directly into the inflamed joint. However, these types of treatments only reduce inflammation for a limited time span. Thus, they are required to be administered regularly by the subject or his/her attending physician.

Recently, however, there have been a number of attempts to develop implants that administer pharmaceutical agents gradually and continuously over a longer time frame. One development has been to use a non-injectable implants such as a depot. A depot is a device that contains and gradually releases a pharmaceutical agent to a targeted region over time. One example of a depot is a capsule that contains the pharmaceutical agent within a biocompatible housing where the end caps of the capsule are comprised of a biodegradable polymer. A second example of a depot is a biodegradable capsule wherein the pharmaceutical agent is distributed homogenously throughout the capsule. With both types of depots, as the biodegradable polymer degrades in the body, the pharmaceutical agent is gradually released.

Some depots can interfere in the movement of the parts of the joints if the depot is placed inside the joint capsule. When that happens, the depot can injure the bone or soft connective tissue within the joint capsule. Instead of alleviating pain and promoting healing, the depot becomes the cause of pain and injury. Thus, there is a need for a depot, which has a shape and is positioned within the joint or next to the joint and can release at least one pharmaceutical agent over a period of time so that the depot allows unfettered movement of the joint while helping the joint heal. In addition, the depot may help prevent or reduce the likelihood of adverse systemic effects of the pharmaceutical agent by having the pharmaceutical agent located at or near the site of injury rather than being administered systemically.

SUMMARY

New drug depot compositions and methods are provided, which can easily allow accurate and precise implantation of a drug depot with minimal physical and psychological trauma to a patient. One advantage of the drug depot compositions and methods is that the drug depot can now be easily delivered to the target tissue site (e.g., synovial joint) with little physical or psychological trauma to the patient. In this way, accurate and precise implantation of a drug depot in a minimally invasive procedure can be accomplished. In various embodiments, the drug depot comprises one or more anchoring members (e.g., barbs, hooks, wire, etc.) that allows accurate placement of the drug depot in a manner to optimize location, accurate spacing, and drug distribution within the joint capsule.

In one embodiment, a method is provided for treating a tissue within a synovial joint in a patient in need of such treatment, the method comprising inserting a drug depot through the synovial joint and attaching the drug depot to the inside of the synovial joint capsule so that the drug depot does not substantially interfere with movement of the joint, wherein said depot comprises a polymer and at least one pharmaceutical agent.

In another embodiment, an implantable drug depot is provided that is useful for treating tissue within a synovial joint in a patient in need of such treatment, the implantable drug depot comprising a therapeutically effective amount of a pharmaceutical agent and a polymer, the depot capable of being attached to an inside of a synovial joint capsule so that the drug depot does not substantially interfere with movement of the joint and the drug depot is capable of releasing the pharmaceutical agent over a period of at least three days.

In one exemplary embodiment, a method of reducing pain and/or inflammation of tissue within a synovial joint is provided, the method comprising inserting a drug depot through the synovial joint and attaching the drug depot to the inside of the synovial joint capsule so that the drug depot allows normal articulation of the synovial joint and does not substantially interfere with movement of the joint, wherein the depot comprises a polymer and at least one analgesic and/or anti-inflammatory agent and the drug depot is capable of releasing the at least one analgesic and/or anti-inflammatory agent over a period of at least three days.

In another exemplary embodiment, an implantable drug depot is provided that is useful for treating tissue within a synovial joint in a patient in need of such treatment, the implantable drug depot comprising a therapeutically effective amount of a pharmaceutical agent and a polymer, the depot comprising one or more anchoring members capable of being attached to an inside of a synovial joint capsule so that the drug depot does not substantially interfere with movement of the joint and the drug depot is capable of releasing the pharmaceutical agent over a period of at least three days, wherein the one or more anchoring members (i) swells when it comes in contact with a bodily fluid or (ii) folds, compresses, or rolls in a first state and unfolds, uncompresses, or unrolls in a second state after the drug depot is inserted into the inside of the synovial joint.

BRIEF DESCRIPTION OF THE FIGURES

In part, other aspects, features, benefits and advantages of the embodiments will be apparent with regard to the following description, appended claims and accompanying drawings where:

Figure 1:
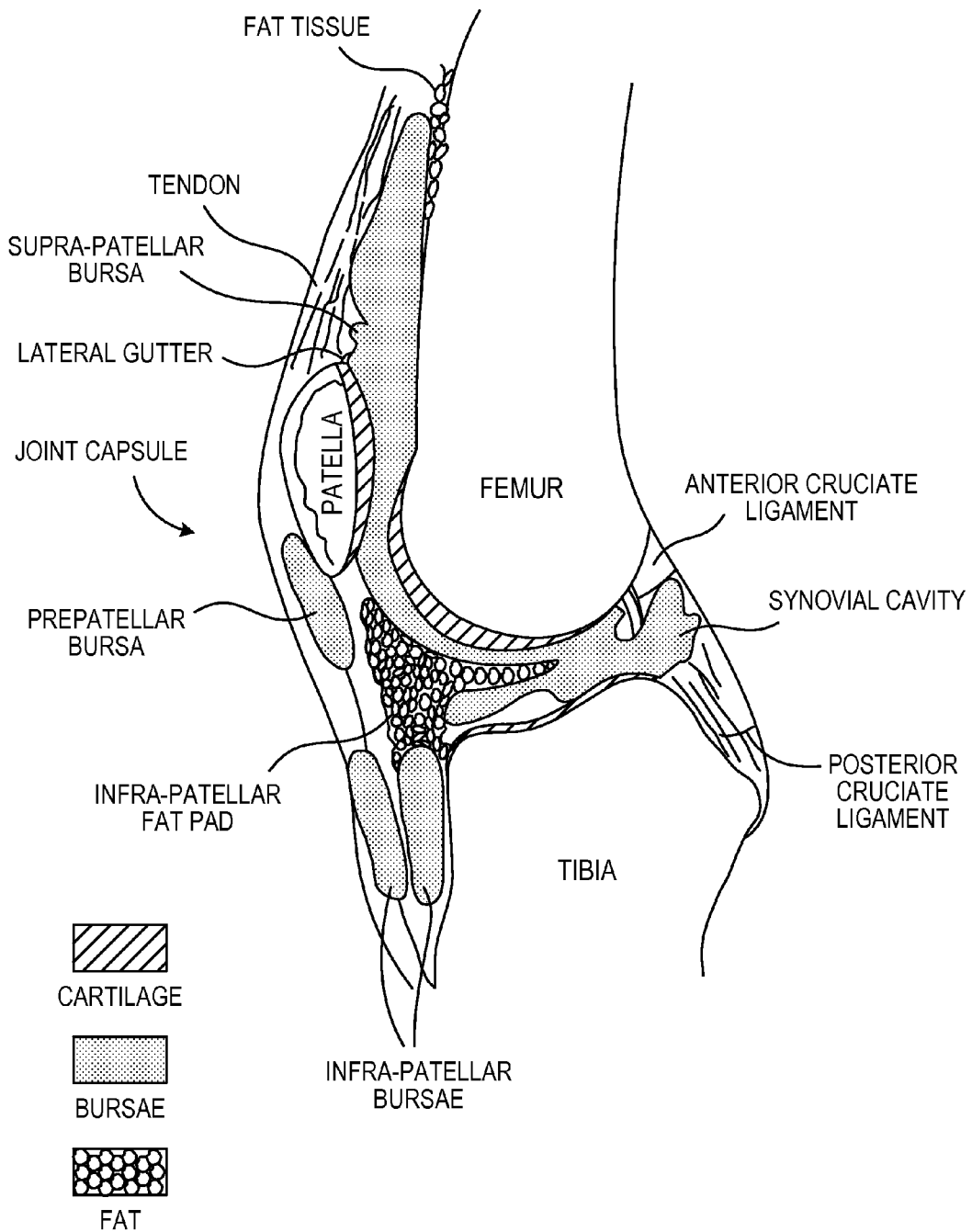
FIG. 1 illustrates a side sectional view of a joint capsule with different tissue types that are treatable with the one or more drug depots.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

DEFINITIONS

The term "treating" or "treatment" of a disease refers to executing a protocol, which may include administering one or more pharmaceutical agents to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and at least one analgesic agent or its pharmaceutically acceptable salt. The dosage administered to an individual, as single or multiple doses, can vary depending upon numerous factors, including the pharmaceutical agent's pharmacokinetics, the route of administration, the patient's condition and characteristics (sex, age, body weight, health, size, etc.), symptoms, concurrent treatments, frequency of treatment, and the effect desired.

"Localized" delivery is defined herein as non-systemic delivery wherein a pharmaceutical agent is deposited within a tissue, for example, inside a joint capsule, or in close proximity thereto.

One or more "anchoring member(s)" or "attachment member(s)" holds the depot in place within the joint capsule or on the interior of the capsular bursae. The anchoring member comprises an exterior and interior surface, the exterior surface of the anchoring member capable of contacting the tissue in the joint capsule. In various embodiments, the anchoring member comprises barbs, clips, latch, staples, rivets, adhesives, sutures, or the like that retain the drug depot to the inside of the joint capsule. In various embodiments, the anchoring member has radially compressed and radially expanded support frame configurations. Such an anchoring member can be implanted at a point of treatment within the joint capsule by minimally invasive techniques, such as a delivery and deployment through a catheter or arthroscopic device. In various embodiments, the entire drug depot can be folded, rolled, and/or compressed in a delivery system and when deployed at the implant site, expands to hold itself at the desired site. For example, the anchoring member can exert a radially outward force on the interior of the tissue at the point of implantation in the body. Examples of metals suitable for use in the anchoring member include, but are not limited to, molybdenum alloys, stainless steel, spring steel (e.g. Elgiloy®), shape memory alloy, and/or nitinol, which are considered desirable materials for use in the anchoring member due at least to their biocompatibility, shapeability, and well-characterized nature.

"Substantially interfere" includes moderate to severe interference with the articular movement of the joint, which causes pain and/or inflammation. In various embodiments, after the drug depot is implanted, there may be mild or no interference with articulating movement of the joint. This can be accomplished, by, among other things, placing the depot at the desired location (e.g., inside the synovial membrane), using a depot of the appropriate size and shape.

In various embodiments, an apparatus and methods for providing treatment within a synovial joint are provided. The treatment comprises administering to the synovial joint of the subject in need of treatment a pharmaceutically effective amount of at least one pharmaceutical agent, which are contained in an implant (referred to here as a "depot"). The depot can release the at least one pharmaceutical agent in a sustained-release manner (i.e., over long period of time) or in a non-sustained release manner (i.e., over a short period of time).

In a particular embodiment of the present invention, the at least one pharmaceutical agent include, but not are limited to, anti-inflammatory agents, anti-infective agents (such as, antibiotics, antiviral agents, anti-protozoal agents, anti-fungal agents, and anti-parasitic agents), analgesics, growth factors, cytokines, lubricants, nutrients, or other joint therapy agents. As discussed herein, a pharmaceutical depot can be inserted into a synovial joint capsule such as, but not limited to, the knee, through the synovial membrane. The depot can be secured to the inside of synovial membrane by a variety of attachment devices, such as sutures, barbs, tacks, staples, tethers, and adhesives.

FIG. 1 illustrates a side sectional view of a joint capsule with different tissue types that are treatable with the one or more drug depots. FIG. 1 illustrates an exemplary synovial joint where the drug depot may be implanted so as not to substantially interfere with movement of the joint. Shown is the synovial joint for the knee. However, it will be understood that the drug depot may be implanted in any synovial joint (e.g., fingers, toes, etc.). Exemplary areas to implant the drug depot, include, but are not limited to, fat tissue, tendon, lateral gutter, supra-patellar or prepatellar bursa, infra-patellar fat pad, infra-patellar bursa, infra-patellar bursa, anterior cruciate ligament, posterior cruciate ligament, trochlear groove, meniscus, or region around the meniscus, cartilage, femur, tibia and/or synovial membrane of a knee (which surrounds the synovial joint) so long as the depot does not substantially interfere with movement of the joint.

Figure 2:
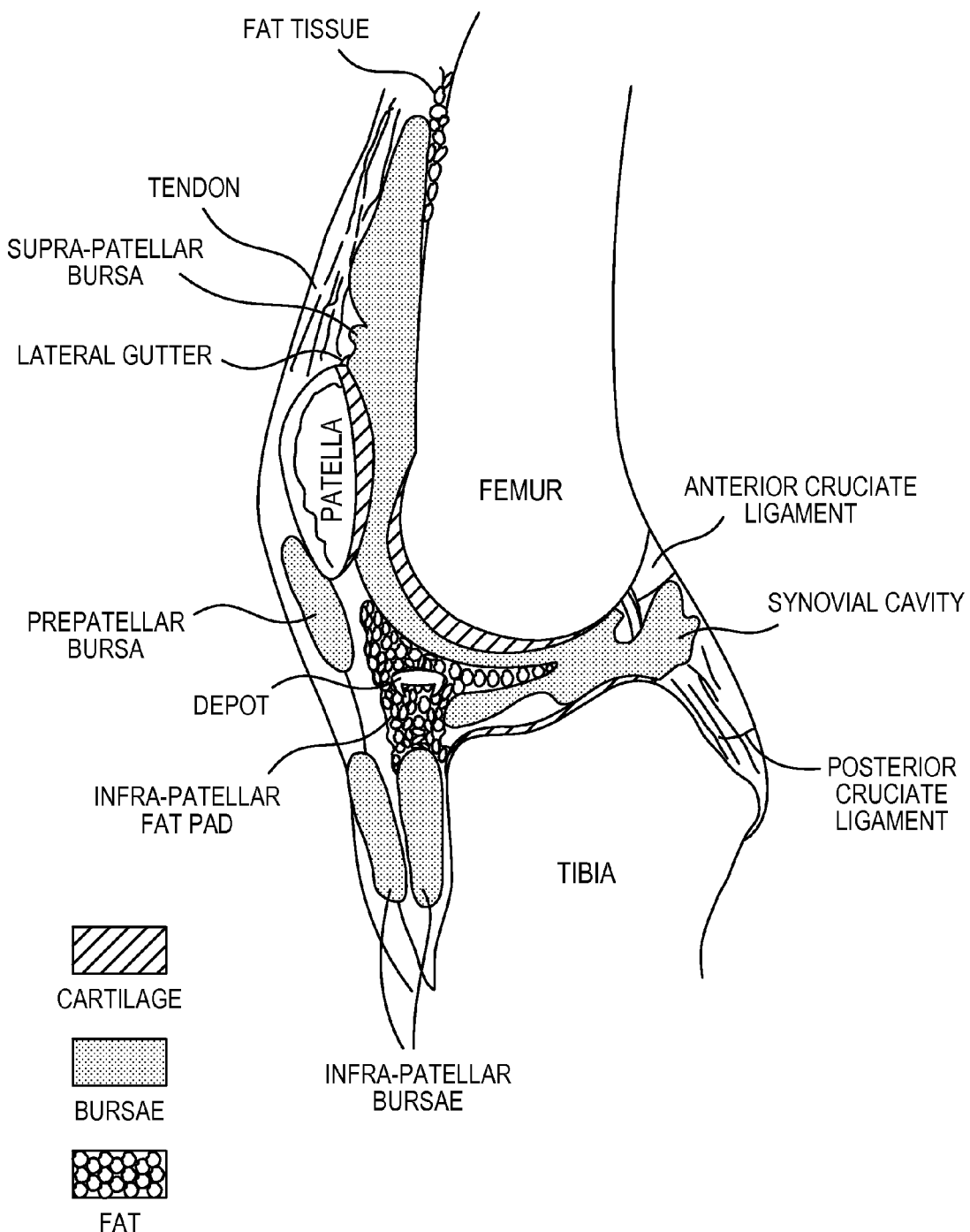
FIG. 2 illustrates a side sectional view of a joint capsule with different tissue types that are treatable with the one or more drug depots. In this view a drug depot containing barbs as the anchoring member is implanted within the infra-patella fat pad of the joint capsule.

FIG. 2 illustrates a side sectional view of a joint capsule with different tissue types that are treatable with the one or more drug depots. In this view a drug depot containing barbs as the anchoring member is implanted within the infra-patellar fat pad of the joint capsule.

Alternatively, the depot can be attached to the outside of the synovial membrane and release the pharmaceutical agent into the surrounding tissue. Then the pharmaceutical agent can diffuse through the synovial membrane to provide therapeutic affects within the joint capsule. Diffusion of the pharmaceutical agent may also occur into the surrounding synovial fluid of the joint space. The depot may be manufactured to allow for diffusion only into the capsular region or only into the joint space.

In another embodiment, the depot can be placed inside the joint capsule such that the depot does not move, for example, placed in the supra-patella or prepatella bursa or inner membrane of the joint cavity of the knee. When appropriate, the implant may be placed in the subpatellar fat or intrapatellar bursa (e.g., to treat inflammation in the areas around these sites).

Figure 2A:
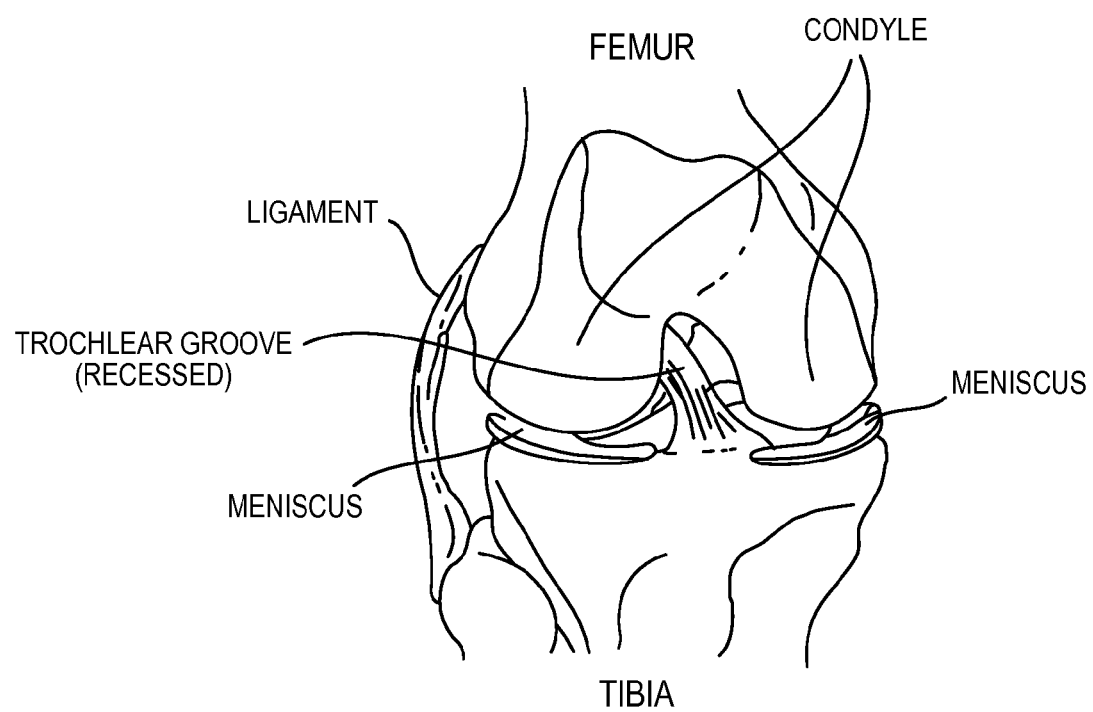
FIG. 2A illustrates a front view of a joint capsule with different tissue types that are treatable with the one or more drug depots.
Figure 2B:
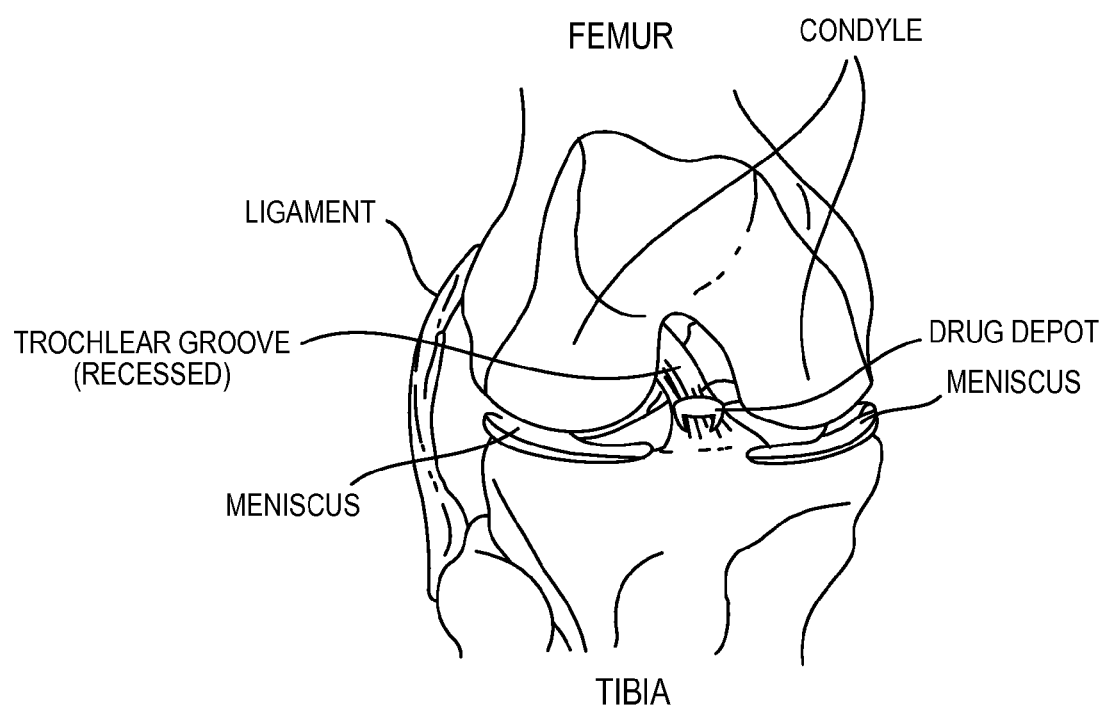
FIG. 2B illustrates a front view of a joint capsule with different tissue types that are treatable with the one or more drug depots. In this view a drug depot containing barbs as the anchoring member is implanted within the trochlear groove of the joint capsule.

FIG. 2A illustrates another embodiment of a front view of a joint capsule with different tissue types that are treatable with the one or more drug depots. FIG. 2B illustrates a front view of a joint capsule with different tissue types that are treatable with the one or more drug depots. In this view a drug depot containing barbs as the anchoring member is implanted within the trochlear groove of the joint capsule.

The depot has a shape and is positioned inside or outside the joint in such a manner as to allow for normal joint articulation. Normal joint articulation may be defined as, but is not limited to, the range of motion of the joint if not depot was present (interring with the movement of the joint). The depot will be capable of carrying at least one pharmaceutical agent in quantities sufficient for therapeutic or prophylactic treatment over a pre-selected period of time. The depot may also protect the at least one pharmaceutical agent from premature degradation by body processes (such as proteases) for the duration of treatment. The sustained-release of the at least one pharmaceutical agent will result in local, biologically effective concentrations of the at least one pharmaceutical agent in or around an inflamed or infected joint.

The depots and methods provided, in various embodiments, allow for long term, sustained release of at least one pharmaceutical agent. The depot can release the pharmaceutical agent over 1 day, 2 days, 3 days, 4 days, 5 days, 10 days, 15 days, 20 days, or 30 days. In an alternative embodiment, the depot can release the at least one pharmaceutical agent over 30 days, 60 days, 90 days, 180 days, 6 months, 9 months, 12 months, 14 months, 16 months, or 18 months. In another embodiment, the depot can contain two or more pharmaceutical agents, each one being released over different number of days or months.

In various embodiments, a pharmaceutical depot is designed for long term use to treat diseases of a joint. In particular the depot's shape and place of attachment allow for unfettered movement of the bones, ligaments, tendons and other body parts within the joint. The depot contains at least one pharmaceutical agent. Because the depot is located inside or adjacent to the joint capsule, the effective dose of the pharmaceutical agent can be lower than the effective dose of the same pharmaceutical agent administered systemically. This ability to use a lower effective dose and to have the pharmaceutical agent localized to the site of the injury or disease results in a reduction of the likelihood of adverse effects of the pharmaceutical agent. It is known that systemic, long-term administration of some pharmaceutical agents results in adverse effects, such as liver toxicity, weight gain, weight loss, muscle wasting, kidney damage, and cardiac damage. By locating a depot at or near the site of injury or disease, the localized drug level may be sufficiently high to treat the injured or diseased joint tissue, but sufficiently low enough in tissue distant from the site to prevent side effects or toxicity.

In various embodiments, the pharmaceutical agent is provided in the drug depot to deliver about 1 pg/kg/day to 1 mg/kg/day of the drug.

Clonidine

In one embodiment, the anti-inflammatory agent is clonidine, also referred to as 2,6-dichloro-N-2-imidazolidinyldenebenzenamine. Clonidine or a pharmaceutically acceptable salt thereof is available from various pharmaceutical manufactures.

The dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 µg/day. In some embodiments, the amount of clonidine is between 40 and 600 µg/day. In some embodiments, the amount of clonidine is between 200 and 400 µg/day.

Fluocinolone

In one embodiment, the anti-inflammatory agent comprises fluocinolone or a pharmaceutically acceptable salt thereof such as the acetonide salt. Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.0005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 μg/day. In some embodiments, the amount of fluocinolone is between 40 and 600 μg/day. In some embodiments, the amount of fluocinolone is between 200 and 400 μg/day.

In various embodiments, provided are methods, systems and compositions for decreasing, eliminating, or managing pain, especially pain of neuromuscular or skeletal origin, by providing direct and controlled delivery, i.e., targeted delivery of at least one pharmaceutical agent to one or more sites of inflammation and sources of pain. A pharmaceutical agent itself may be on a continuum of rapid acting to long acting compositions. Generally, the pharmaceutical agent is a component of a pharmaceutical composition, which can range in a continuum of rapid release to sustained release. Still further, the delivery of that pharmaceutical composition via a depot can include, for example, rapid and repeating delivery at intervals or continuous delivery. The delivery can be local, direct, and controlled. A pharmaceutical composition contains at least one pharmaceutical agent, diluents, carriers, and excipients. Diluents, carriers, and excipients are well-known the art.

The depot of this invention has a "low profile" shape, which allows for unrestricted movement of the joint. In various embodiments, the low profile of the depot minimizes volume displacement if placed in the synovial space. The "low profile" shape of the depot means that the depot's height is minimized. The length and width of the depot can range from about 1 mm to about 35 mm. The height of the depot can range from about 0.1 mm to about 1.5 mm. Because the height is minimized as compared to the length and width, the depot's shape can be referred to as a sheet, ribbon, fiber, disc, thread, wafer, or other similar shapes. In one embodiment, the depot can have small voids randomly present throughout the depot, thus giving the appearance of a mesh, sponge, or similar item. When attached to the inside of the joint membrane or placed in the upper lateral gutter of the knee (the lateral gutter of the knee is the region posterior to the patella (shown in FIGS. 1 and 2), this low profile depot allows for normal articulation of the joint.

Figure 8:
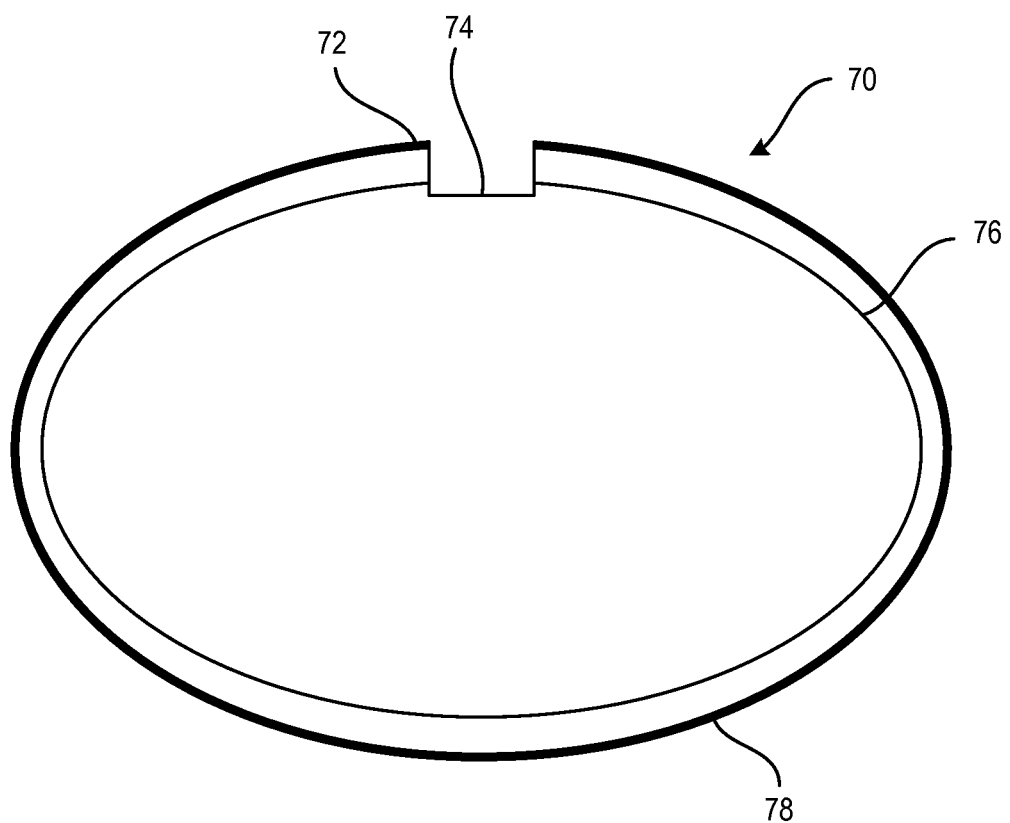
FIG. 8 is a side sectional view of an oval shaped drug depot that contains a chamber for filing the pharmaceutical agent within the drug depot.

In another embodiment, the low profile depot contains an internal void that holds the at least one pharmaceutical agent or a pharmaceutical composition which contains the at least one pharmaceutical agent. The pharmaceutical agent(s) can pass through the walls that define the internal void in a controlled release manner. One can view this embodiment of the depot as a balloon, but a balloon with a low profile whereby its height is minimized compared to its width and/or length. Even with this internal void, this depot does not interfere with the movement of the connective tissue within the joint when securely attached to the joint membrane or placed in an upper synovial bursa of the knee. FIG. 8 is a side sectional view of an oval shaped drug depot 70 that has an exterior surface 78 that allows release of the pharmaceutical agent as fluid contacts the depot. The exterior surface of the depot comprises a channel 74 that allows the drug depot to be filled with the pharmaceutical agent. It will be understood that the drug depot may have a closure member to close channel 74. For convenience, in this embodiment, the channel is in an open position.

The depot can be flat or have some curvature to it. In one embodiment of this invention, the depot is shaped to mimic the curvature of a synovial joint membrane. In this manner, the depot can be placed along the inside of the synovial joint membrane and not protrude or extend too much into the joint space. Thus, the depot does not interfere with the movement of the connective tissue within the joint. Alternatively, the depot can be placed on the outside of the synovial joint, attached to the membrane, and not project into the surrounding tissue. In this manner, the depot would not interfere with the movement of the tissue around the joint. When the depot is flat, it has flexibility to bend and take the shape in which it is positioned.

One can place the depot in any part of a synovial joint, along the internal side of the capsular membrane or on the outside of the capsular membrane. When placed next to the membrane, it may be advantageous to attach the depot to the membrane so that the depot remains securely attached to the membrane to allow for normal articulation of the joint. The depot can be secured to the synovial membrane by a variety of attachment devices, such as sutures, barbs, tacks, staples, tethers, and adhesives. Certain attachment devices, such as sutures, barbs, tacks, staples, and tethers, can be attached to the depot prior to inserting the depot into the patient, and then passed through the synovial membrane in such a manner as to secure the depot to the synovial membrane. Alternatively, one can place the attachment devices through the joint membrane and the depot in order to securely attach the depot to the joint membrane.

In addition, attachment devices such as sutures, barbs, tacks, staples, and tethers, can absorb fluid when inside the body and swell, thereby helping to secure the depot to the membrane.

In some embodiments, the drug depot comprises microspheres that release the pharmaceutical when they come in contact with a bodily fluid or sprayed dried single or double emulsions. In some embodiments, the drug depot comprises a hydrogel or a hydrogel combined with microspheres that are sprayed on the depot.

Figure 3:
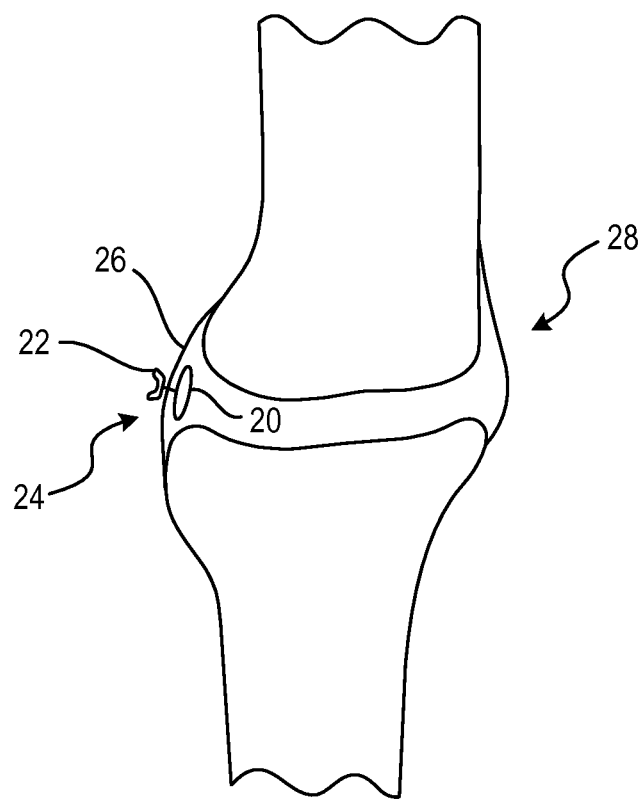
FIG. 3 illustrates a front sectional view of the drug depot sutured to the synovial membrane of the joint capsule.

FIG. 3 illustrates an embodiment of a drug depot 20 anchored to the inside of the joint capsule 28 held against the inside of the synovial membrane 26 by sutures 22. It is contemplated that the several drug depot designs may be used in joint capsules, with one or more sutures being used to retain the drug depot up against the inside of the joint capsule. FIG. 3 shows, for example, deployment of the implant in a synovial joint. The tip of the depot may be designed to ease insertion of the depot through the joint capsule tissue and minimizes tissue disruption. A very small hole 24 is made in the joint capsule with a blunt probe, and then the tapered rod is slowly pushed through this hole, slowly stretching the tissues apart to minimize tissue tearing. Once the rod is fully inserted, the hole in the joint capsule 24 closes upon itself. The suture 22 embedded in the rod is left passing through the capsule so that it can be pulled taught and knotted up against the outside of the joint capsule, forcing the depot up against the inside of the joint capsule. Having the depot up against the inside of the joint capsule will prevent the depot from interfering with normal joint motion.

Figure 4A:
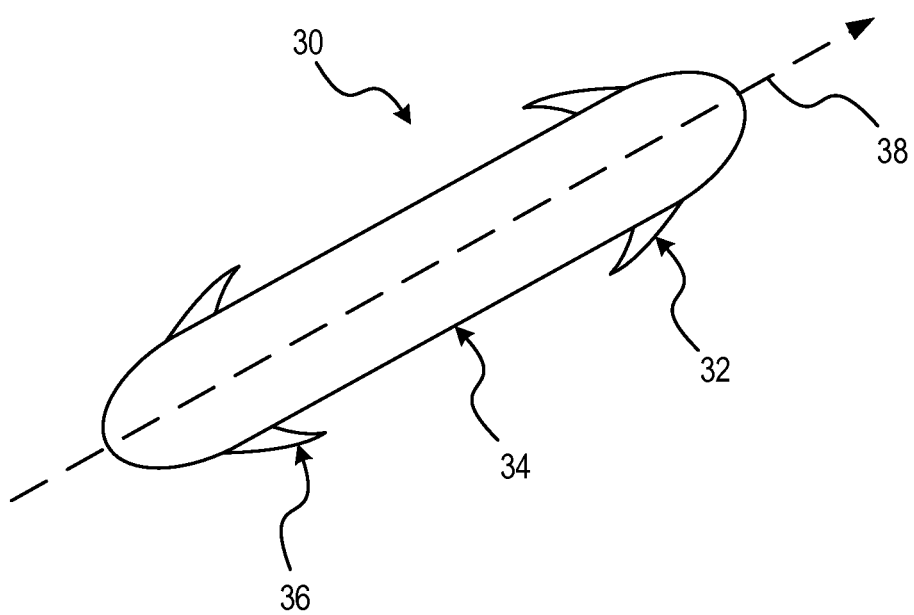
FIG. 4A illustrates a side view of an embodiment of the drug depot having barbs as the anchoring members.

FIG. 4A illustrates a side view of an embodiment of a drug depot 30. The drug depot 30 may be solid or semi-solid. The drug depot 30 has a rod-shaped outer surface 34 from which a therapeutic agent, contained internally of the outer surface 34, diffuses. Extending from the outer surface 34 are one or more first barbs 32 and one or more second barbs 36. The first barbs 32 point backwards along the longitudinal axis 38 to prevent backward movement of the drug depot 30 (e.g., movement opposite to the direction indicated by longitudinal centerline arrow 38); the second barbs 36 point forwards along the longitudinal axis 38 to prevent forward movement of the drug depot 30 (e.g., movement along the longitudinal centerline arrow 38). The barbs 32 and 36 thus serve as an anchoring system to keep the drug depot 30 at the targeted delivery site; that is, the anchoring systems prevent both forward and backward translational movement of the drug depot 30.

Swellable Depots

Figure 4B:
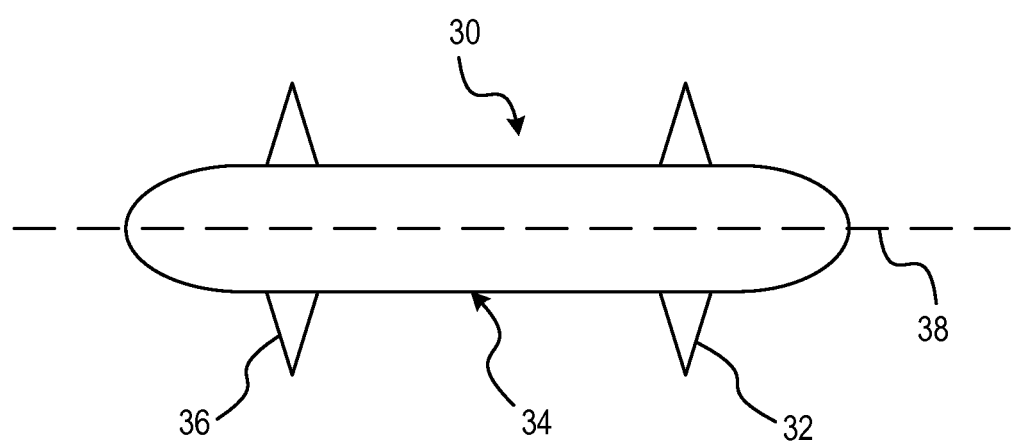
FIG. 4B illustrates a side view of an embodiment of the drug depot having swellable barbs as the anchoring members.

FIG. 4B illustrates a side view of a drug depot 30 held in place by swellable barbs (shown swollen after contact with bodily fluid (e.g., interstitial fluid, blood, etc.). The swellable barbs further anchor the drug depot to the target site. The drug depot 30 has a rod-shaped outer surface 34 from which a therapeutic agent, contained internally in the depot, diffuses out of the outer surface 34. Extending from the outer surface 34 are one or more first barbs 32 and one or more second barbs 36. The first barbs 32 point backwards along the longitudinal axis 38 to prevent backward movement of the drug depot 30 (e.g., movement opposite to the direction indicated by longitudinal centerline arrow 38); the second barbs 36 point forwards along the longitudinal axis 38 to prevent forward movement of the drug depot 30 (e.g., movement along the longitudinal centerline arrow 38). The barbs 32, 36 thus serve as an anchoring system to keep the drug depot 30 at the targeted delivery site; that is, the anchoring systems prevent both forward and backward translational movement of the drug depot 30.

The swellable anchoring members comprise polymers that will swell upon taking in fluid (e.g., saline, water, bodily fluid, etc.)—thus increasing the volume of the anchoring member and which further holds the drug depot in position over time.

The swellable anchoring members may comprise polymers, monomers, starches, gums, poly(amino acids) or a combination thereof that swell upon contact with fluid (water, saline, body fluids, etc). In various embodiments, the amount of swelling can range from 5 to 100 percent, 5 to 40 percent, or 5 to 20 percent. The time to reach maximum swelling can be designed into the design of the product. In practice, the time to reach maximum swelling can occur within a period of 5 days, 3 days, 2 days or within a period of 24 hours.

Nonlimiting list of swellable materials from which the anchoring member may be made include polyvinyl alcohol (PVA), PVA modified with hydrophilic co-monomers, e.g. AMPS, PVA modified with fast crosslinking groups, e.g. NAAADA, PVA modified with polyvinylpyrroline (PVP), polyethylene glycol (PEG), poly(vinyl ether), co-polymers of PVA and PEG, polypropylene glycol (PPG), co-polymers of PEG and PPG, co-polymers of PVA or PPG, polyacrylonitrile, hydrocolloids, e.g. agar, alginates, carboxymethylcellulose (CMC), collagen, elastin, chitin, chitosan, gelatin, or the like. In various embodiments, the swellable material includes, for example, poly(N-isopropylacrylamide-co-acrylic acid)-poly(L-lactic acid) (NAL); poly(N-isopropyl acrylamide) (PNIPAM) grafted to other polymers such as carboxymethylcellulose (CMC) copolymers or polymers including block copolymers and end-functionalized polymers, composites or copolymers containing thermo-sensitive poly(2-ethoxyethyl vinyl ether) and/or poly(hydroxyethyl vinyl ether) and/or (EOVE200-HOVE400), whose sol-gel transition temperature is 20.5° C. The swellable material, in various embodiments, may be used to control release of the drug into the tissue and/or the synovial space.

The polymers may be crosslinked, lightly crosslinked hydrophilic polymers. Although these polymers may be non-ionic, cationic, zwitterionic, or anionic, in various embodiments, the swellable polymers are cationic or anionic. In various embodiments, the swellable polymer may contain a multiplicity of acid functional groups, such as carboxylic acid groups, or salts thereof. Examples of such polymers suitable for use herein include those which are prepared from polymerizable, acid-containing monomers, or monomers containing functional groups which can be converted to acid groups after polymerization. Examples of such polymers also include polysaccharide-based polymers such as carboxymethyl starch and cellulose, and poly(amino acid) polymers such as poly(aspartic acid). Some non-acid monomers may also be included, usually in minor amounts, in preparing the absorbent polymers. Such non-acid monomers include, for example, monomers containing the following types of functional groups: carboxylate or sulfonate esters, hydroxyl groups, amide groups, amino groups, nitrile groups, quaternary ammonium salt groups, and aryl groups (e.g. phenyl groups, such as those derived from styrene monomer). Other potential non-acid monomers include unsaturated hydrocarbons such as ethylene, propylene, 1-butene, butadiene, or isoprene.

The swellable anchoring member may be dehydrated and swell after implantation in response to fluid uptake. The anchoring member may be fully dehydrated or only partially dehydrated. Upon exposure to liquid (water, saline, body fluids, etc.), the anchoring member will absorb the liquid and swell. In some instances, the design of the drug depot may allow the anchoring member to swell with sufficient force despite being constrained to provide both space filling and expansion to hold the depot in place. In some embodiments, the anchoring member can swell by incorporating fluid having differences in ionic strength between the exterior and interior of the anchoring member.

In various embodiments, the body of the depot or tether is swellable and/or the anchoring members are swellable to elute the API, when the depot is injected, implanted and/or deployed at or near the target tissue site.

Figure 5A:
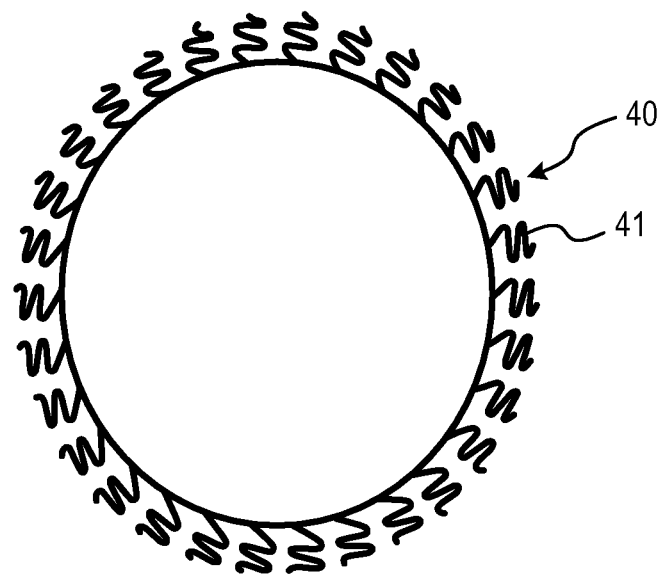
FIG. 5A illustrates a side view of an embodiment of a circular drug depot with corkscrew anchoring members.
Figure 5B:
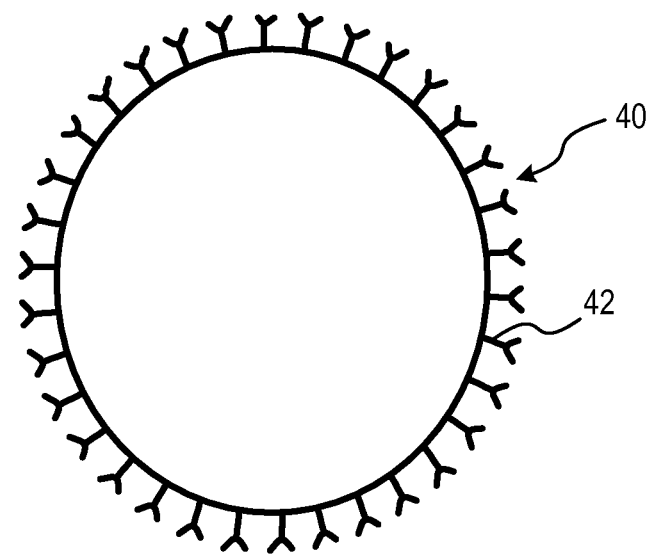
FIG. 5B illustrates a side view of an embodiment of a circular drug depot with fish hook anchoring members.

FIG. 5A illustrates a side view of an embodiment of a circular drug depot 40 with cork screw anchoring members 41 disposed on the exterior surface of the drug depot. The interior of the drug depot contains a therapeutically effective amount of the pharmaceutical agent. The cork screw anchoring members reduce or prevent migration of the drug depot from the desired location. For example, the cork screw anchoring members prevent backward or forward movement of the drug depot. FIG. 5B illustrates a side view of an embodiment of a circular drug depot 40 with fish hook anchoring members 42 disposed on the exterior surface of the drug depot. The interior of the drug depot contains a therapeutically effective amount of the pharmaceutical agent. As with the cork screw anchoring members, the fish hook anchoring members reduce or prevent migration of the drug depot from the desired location.

In one embodiment, the depot is manufactured with the attachment devices as an integral part of the depot. In another embodiment, the attachment devices are connected to the depot prior to insertion of the depot into a patient. In the third embodiment, the attachment devices are connected to the depot after the depot is placed in the patient's body.

One can attach the depot to the synovial membrane at the corners of depot, in the middle of the depot, or at any other place(s) in or on the depot. For example, one can suture the corners of the depot to the membrane or suture along one, two, three or more sides of the depot (depending on the depot's shape). Or one can suture the depot to the membrane in one, two, three, or more spots on the depot. The placement of the attachment devices may depend on several factors, including, but not limited to, if the entire depot is likely to remain in close proximity to the synovial membrane so that the depot does not interfere with the movement of the joint's components, and/or the ease of attaching the depot at multiple sites to the membrane so as not to damage the cartilage, exposed bone, meniscus, or tendons due to rubbing or friction.

The placement of the depot may utilize a self-centering mechanism consisting of smart memory alloy SMA connectors or springs that attach across the width of the depot, such as might occur when the depot is in the delivery format of a folded, expandable, sheet, ribbon, or patch. These attached springs may be made of copper-zinc-aluminum-nickel, or nickel-titanium, copper, nitinol, or other blends of martensite materials.

Figure 6C:
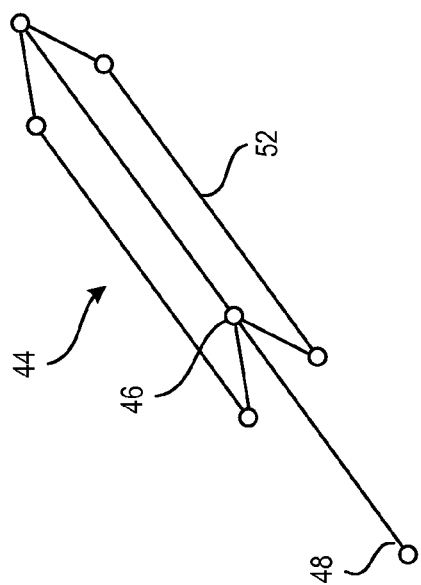
FIGS. 6A, 6B, and 6C, respectively, illustrate a longitudinal view of a collapsible or foldable drug depot in a first compressed or folded state, an expanded or unfolded state and a second compressed or folded state.
Figure 6B:
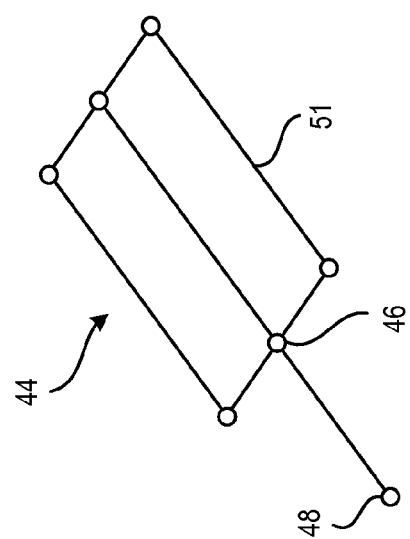
Figure 6A:
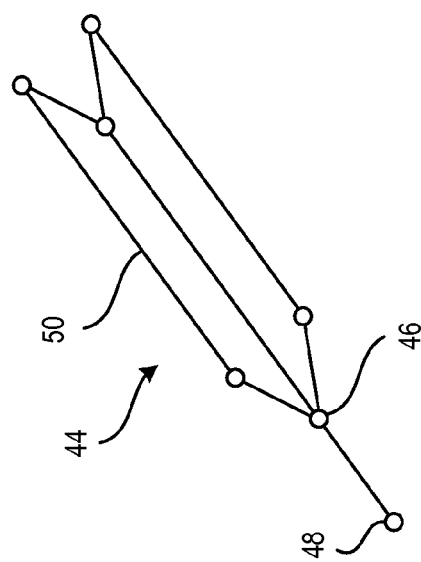

FIGS. 6A, 6B, and 6C, respectively, illustrate a longitudinal view of a foldable or collapsible drug depot (frame shown in 44). In this embodiment, the drug depot comprises shape memory alloys, or nitinol wires and is in a first radially compressed state 50, a radially expanded state 51 and a second radially compressed state 52, respectively. For purposes of simplicity, the collapsible drug depot in FIGS. 6A, 6B and 6C has been depicted with only two proximal arms, two distal arms and two outer struts. As will be understood by one skilled in the art, additional proximal arms, distal arms and outer struts are possible. In the first compressed state 50, the proximal arms may be pivoted and folded substantially parallel to each other and pulling tether 48 will open or unfold the depot to the expanded state 51 along an axis 46 so that the arms are planar to each other. This will cause the drug depot to be anchored against the desired tissue and prevent unwanted migration of the drug depot to distant sites. Pulling the tether further will cause the drug depot arms to be in a second compressed state 52 which will allow the arms to anchor against select tissue, as they will be substantially parallel to one another along axis 46. It will be understood that depending on the location that the drug depot may be placed, in various embodiments, the expanded, first radially compressed or second radially compressed states may be employed before, during or after deployment of the depot from the catheter or needle.

Adhesive

An "adhesive" is any substance that is sticky and helps one item to stick to another. Examples of adhesives include, but are not limited to, glycerin, polyethylene glycol (PEG), Bio-Glue® surgical adhesive (CryoLife, Inc., Kennesaw, Ga.) which is a combination of purified bovine serum albumin (BSA) and glutaraldehyde, DermaBond® (Ethicon, Inc., New Brunswick, N.J.) which contains 2-octyl cyanoacrylate, VetBond (3M, MN) which contains n-butyl cyanoacrylate, Indermil (Tyco), Tissumend II (VPL) which consists of methoxypropyl cyanoacrylate, fibrin, or adhesive hydrogels such as chitosan hydrogels, a hydrogel of gelatin and poly(L-glutamic acid) combined with a water-soluble carbodiimide, 2-butyl cyanoacrylate, or combinations thereof.

An adhesive can be applied to the depot during manufacturing of the depot, just prior to insertion of the depot into the patient's body, or after insertion of the depot into the patient's body. An adhesive may be applied along the ends or near the ends of the depot. Alternatively, an adhesive can be applied to several spots on the depot or along the entire surface of the depot that faces the membrane. After the depot is inside the synovial membrane, one can move it into position next to the synovial membrane and press it against the membrane for the appropriate amount of time so that the adhesive will cure and securely attach the depot to the membrane.

In one embodiment, when one is placing the depot inside the knee joint, one may place the depot in the upper lateral gutter. The benefits of placing the depot in the upper lateral gutter include delivery to aspects of the joint that are most likely to be damaged by injury or arthritis. For example, this bursal space is continuous with the patellar and femoral and tibial compartments of the knee, thus allowing for contact of eluting drug with all the cartilaginous surfaces of the joint (see FIGS. 1 and 2).

Alternatively, one can attach the depot to the synovial membrane on the outside of the synovial joint. When the at least one pharmaceutical agent is released from the depot, it can treat the surrounding tissue and/or diffuse through the synovial membrane to treat the tissue inside the joint.

The depot may be made from polymers; biodegradable (also referred to as "resorbable" polymers) and/or non-biodegradable polymers can be used. These polymers are useful because of their versatile degradation kinetics, safety, and biocompatibility profiles. The polymers can be manipulated to modify the pharmacokinetics of the least one pharmaceutical agent contained within the depot, to shield the pharmaceutical agent from enzymatic attack, as well as degrade over time at the site of attachment such that the pharmaceutical agent is released over time.

Natural biodegradable polymers include, but are not limited to, proteins (e.g., collagen, albumin, elastin, silk, glycosaminoglycans, chondroitin sulfate, or gelatin); polysaccharides (e.g., cellulose, cellulose starch, starch, alginates, chitin, chitosan, cyclodextrins, polydextrose, dextrans, glucosamine, hyaluronic acid, or hyaluronic acid esters) or lipids.

Examples of resorbable polymers include, but are not limited to, poly(alpha-hydroxy acids), poly(lactide-co-glycolide) (PLGA), polylactide (PLA), polyglycolide (PLG), polyethylene glycol (PEG), PEG conjugates of poly($\alpha$-hydroxy acids), polyorthoesters, polyaspirins, polyphosphazenes, vinylpyrrolidone, polyvinyl alcohol (PVA), PVA-g-PLGA, polyethylene glycol-terephthalate and polybutylene-terephthalate (PEGT-PBT) copolymer (polyactive), methacrylates, poly(N-isopropylacrylamide), polyethylene oxides (as known as polyoxyethylene or PEO), poly-propylene oxide (also known as polyoxypropylene or PPO), poly (aspartic acid) (PAA), PEO-PPO-PEO (Pluronics®, BASF), PEO-PPO-PAA copolymers, PLGA-PEO-PLGA, polyphosphoesters, polyanhydrides, polyester-anhydrides, polyamino acids, polyurethane-esters, polyphosphazines, polycaprolactones, polytrimethylene carbonates, polydioxanones, polyamide-esters, polyketals, polyacetals, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyorthocarbonates, polycarbonates, or copolymers or physical blends thereof or combinations thereof.

More examples of synthetic biodegradable polymers include, but are not limited to, various polyesters, copolymers of L-glutamic acid and gamma ethyl-L-glutamate (Sidman et al., 1983, *Biopolymers* 22:547-556), polyphosphagenes, various hydrogels (see, for example, Langer et al., 1981, *J. Biomed. Mater. Res.* 15:167-277; Langer, 1982, *Chem. Tech.* 12:98-105), and poly-D-(−)-3-hydroxybutyric acid (EP 133, 988). Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Atridox (PLA; periodontal disease), Nutropin Depot (PLGA; with hGH), and the Trelstar Depot (PLGA; prostate cancer).

Other synthetic polymers include, but are not limited to, poly($\epsilon$-caprolactone), poly(3-hydroxybutyrate), poly($\beta$- malic acid) and poly(dioxanone), polyanhydrides, polyurethane (see WO 2005/013936), polyamides, polyorthoesters, n-vinyl alcohol, polyethylene oxide/polyethylene terephthalate or Dacron®, polyphosphate, polyphosphonate, polydihydropyran, and polyacytal.

In various embodiments, the drug depot comprises poly (lactide-co-glycolide) (PLGA), polylactide (PLA), polyglycolide (PGA), D-lactide, D,L-lactide, L-lactide, D,L-lactide-$\epsilon$-caprolactone, D,L-lactide-glycolide-$\epsilon$-caprolactone, glycolide-caprolactone or a combination thereof.

Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-$\alpha$-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyetherurethane, polycarbonate-urethane and silicone polyether-urethane. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene.

Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The depot may also contain shape memory polymers so that the depot can be compressed or folded prior to and during insertion through the capsule member and then be able to uncompress or unfold after the depot is within the joint. For example, a multi-block copolymer of oligo($\epsilon$-caprolactone) diol and crystallisable oligo($\rho$-dioxanone)diol can be used to create a shape memory polymer. This shape memory polymer features two block-building segments, a hard segment and a 'switching' segment, which are linked together in linear chains. The higher-temperature shape is the polymer's 'permanent' form, which it assumes after heating. One component, oligo($\epsilon$-caprolactone)dimethacrylate, furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored such that it can be used in the present invention. The shape memory polymers can be generated such that they return to their original shape with the application of an external stimulus. The external stimulus can be temperature, an electric or magnetic field, light, or a change in pH.

In an alternative embodiment, the depot may have a frame that can fold and unfold so that the depot can be compressed into a smaller shape for insertion into the joint and then expanded once the depot is inside the joint. Examples of such a frame include, for example, BioSTAR catheter and STARFlex occluder and septal repair implant (NMT Medical, Boston, Mass.). This is used for insertion of a closure (patch) over a septal defect in the heart. A frame for insertion of the patch could have self-centering microsprings made of memory alloy such as nitinol, but be retractable and attached by releasable, biodegradable attachments to the polymer. In one embodiment, the depot may be folded as a single umbrella comprised of a matt of electrospun, biodegradable woven fibers containing or coated with drug. Deployment of the folded, umbrella-like matt with attached microsprings to the inner synovial membrane could be similar to deployment of the STARFlex device (see Mullen et al., 2006; Hanusdorf, 2001) but using a catheter introduced during arthroscopic surgery. In various embodiments, matts are deployed with the umbrella shaped depot. The matts may be created by electrospinning, which typically involves using an electrical charge to form a mat of fine fibers.

In some embodiments, the drug depot comprises inflatable anchoring members (e.g., barbs or tubes) that can be inflated with air or fluid (e.g., dextrose, saline, Ringers Lactate, etc.) to fill the barb or tube causing it to expand to further hold the drug depot in position. In some embodiments, all or some of the anchoring members are inflatable. In some embodiments, of the anchoring members that are inflatable, part of or all of the anchoring member is inflatable. For example, the anchoring member may contain a tube within it that once inflated will inflate that part of the anchoring member.

Figure 7A:
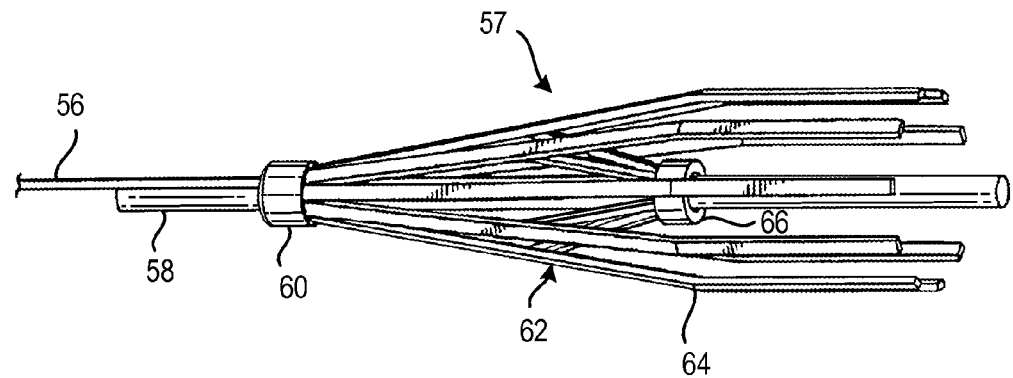
FIG. 7A is a perspective magnified view of one embodiment, depicting in a closed or folded position of an umbrella shaped drug depot, which can expand or unfold using memory shape fibers or expand by pushing a deployment member.
Figure 7B:
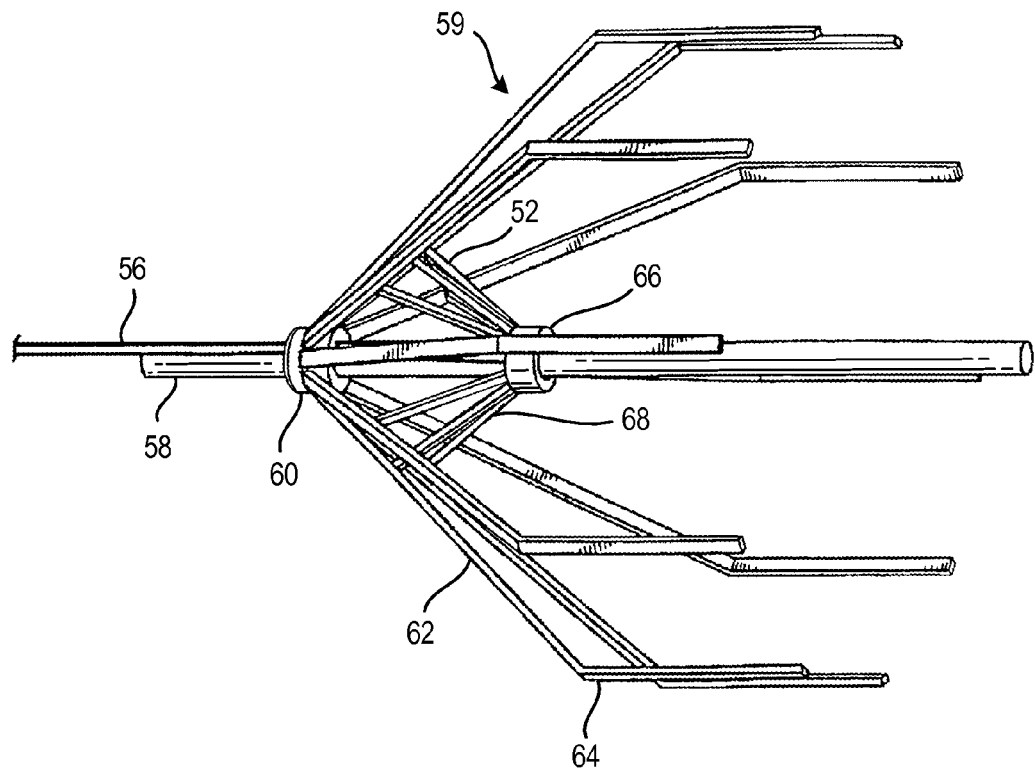
FIG. 7B is a perspective view of one embodiment, depicting in an open position an umbrella shaped drug depot, which is expanded to the open position using memory shape fibers or by pushing a deployment member.

FIG. 7A is a perspective magnified view of one embodiment, depicting in a closed or folded position an umbrella shaped drug depot, which can expand or unfold using memory shape fibers or expand by pushing deployment member 58. The design of the drug depot in this embodiment is similar to that of an umbrella for folding or unfolding to anchor the drug depot to the desired location. The depot comprises frame 56 and optional rings 60 and 66 to hold components in place. The ring may comprise radiographic markers to aid in visualization. As deployment member 56 is pushed, an expandable cage comprising arms 62 and 64 and secondary supporting arm 68 (shown in FIG. 7B) are unfolded and the depot expands. The expanded depot will lodge at or near the target tissue and will be held in place by the expansion. This design allows the depot to be folded in the device for administering the depot and allows the depot to expand after the depot is deployed from the delivery device (e.g., catheter, needle, etc.)

In various embodiments, radiopaque material or markers can be positioned in or on or coated on the depot to assist in determining the position of the depot relative to the inflamed tissue being treated. Examples of radiopaque material include, but are not limited to, barium sulfate, calcium phosphate, iopamidol, iodixanol, gadodiamide, Hypaque® sodium (diatrizoate sodium, Amersham Health, Inc., Princeton, N.J.), Hypaque®-76 (diatrizoate meglumine and diatrizoate sodium, Amersham Health, Inc., Princeton, N.J.), and Hypaque® Meglumine (combination of diatrizoic acid dehydrate, water and meglumine, Amersham Health, Inc., Princeton, N.J.).

Other types of radiopaque material include radioisotopes that can be linked to the depot. Examples of radioisotopes include, $^{18}F$, $^{3}H$, $^{124}I$, $^{125}I$, $^{131}I$, $^{35}S$, $^{14}C$, and $^{11}C$. Radioisotopes may be attached using a chelating agent such as EDTA or DTPA, and can be detected by gamma counter, scintillation counter, PET scanning, or autoradiography.

Alternatively, one can link a fluorescent molecule to the depot. Examples of fluorescent molecules include cy5, cy5.5, fluorescein, fluorescamine, dansyl compounds, ICG, phycoerythryn, phycocyanin, allophycocyanin, o-phthaladehyde, red fluorescent protein, green fluorescent protein and other near infra-red or infra-red fluorophores.

As discussed above, the at least one pharmaceutical agent contained in the depot of this invention can be anti-inflammatory agents, anti-infective agents (such as, antibiotics, antiviral agents, anti-protozoal agents, anti-fungal agents, and anti-parasitic agents), analgesics, growth factors, cytokines, nutraceutical, lubricants, nutrients, or other joint therapy agents.

Anti-inflammatory agents can include cytokines, steroids, non-steroidal anti-inflammatories, and agents that inhibit inflammatory cytokines. Of course, these groups can overlap. Examples of agents that inhibit inflammatory cytokines include, but are not limited to, tumor necrosis factor alpha (TNF-α) inhibitors (for example, onercept, adalimumab, infliximab, etanercept, pegsunercept (PEG sTNF-R1), sTNF-R1, CDP-870, CDP-571, CNI-1493, RDP58, ISIS 104838, 1→3-β-D-glucans, lenercept, PEG-sTNFRII Fc mutein, D2E7, afelimomab and antibodies or antibody fragments that bind to TNF-α or that bind to its receptor), inhibitors of TNF-α production or release (for example, thalidomide, tenidap, and phosphodiesterase inhibitors, such as, but not limited to, pentoxifylline and rolipram, and TNF-alpha converting enzyme inhibitors (TACE)), inhibitors of interleukin-1 (IL-1) (for example, anakinra, a recombinant, non-glycosylated form of the human interleukin-1 receptor antagonist (IL-1Ra); Orthokine® (IL-1Ra obtained from human serum), AMG 108 (a monoclonal antibody that blocks IL-1 activity), and any other antibody or antibody fragment that binds to IL-1 or its receptors), inhibitors of IL-6 (for example, tocilizumab (a humanized anti-IL-6 mAb produced by Chugai Pharma USA, LLC, Bedminster, N.J.) or any other antibody or fragment that binds to IL-6 or its receptor), inhibitors of IL-8 (for example, any antibody or antibody fragment that binds to IL-8 or its receptor), and inhibitors of classical or non-classical nuclear factor kappa B (NFκB) pathways (for example, ureido-thiophenecarboxamide derivatives, diferuloylmethane, IKK-1 and IKK-2 inhibitors, proteosomal inhibitors such as Bortezomib, sulindac, dexamethasone, fluocinolone, dithiocarbamate, and sulfasalazine), or clonidine.

Cytokines that have anti-inflammatory activity include but are not limited to interleukin-4 (IL-4) IL-10, IL-11, and IL-13.

The at least one pharmaceutical agent in the depot can also be an inhibitor of a matrix metalloprotease (MMP). Most MMP inhibitors are thiols or hydroxamates. Non-limiting examples of MMP inhibitors include TAPI-1 (TNF-α protease inhibitor) which blocks cleavage of cell surface TNF; TAPI-0, an analog of TAPI-1 that possesses similar efficacy in vitro; TAPI-2 which is inhibits both the activation-induced shedding of L-selectin from neutrophils, eosinophils, and lymphocytes and also inhibits phenylarsine oxide-induced L-selectin shedding; Ac-SIMP-1; Ac-SIMP-2; SIMP-1; SIMP-2; doxycycline; marimastat (Vemalis Plc, Winnersh, United Kingdom); cipemastat (F. Hoffmann-La Roche Ltd, Basel, Switzerland); and tissue inhibitor of metalloproteinases (TIMPs) which include TIMP-1, TIMP-2, TIMP-3 and TIMP-4. Synthetic inhibitors of MMPs generally contain a chelating group which binds the catalytic zinc atom at the MMP active site tightly. Common chelating groups include hydroxamates, carboxylates, thiols, and phosphinyls.

Examples of steroidal anti-inflammatory agents include but are not limited to hydrocortisone, cortisol, hydroxyltriamcinolone, alpha-methyl dexamethasone, dexamethasone-phosphate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluocinolone acetonide, fluocinonide, flucortine butylesters, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone.

Non-limiting examples of non-steroidal anti-inflammatory compounds include acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Suitable analgesics include, without limitation, non-steroid anti-inflammatory drugs, non-limiting examples of which have been recited above. Analgesics also include other types of compounds, such as, for example, opioids (such as, for example, morphine naloxone, codeine, oxycodone, hydrocodone, diamorphine, pethidine, tramadol, tapentadol, or buprenorphine), local anaesthetics (such as, for example, bupivacaine, ropivacaine, mupivacaine, lidocaine and capsaicin), glutamate receptor antagonists, α-adrenoreceptor agonists (for example, clonidine), beta one receptor antagonists (e.g., HOE-140), adenosine, sodium or calcium channel blockers, neurotoxins (BoNT/A Botulinum toxin), TrkA receptor antagonists, canabinoids, cholinergic and GABA receptors agonists, and different neuropeptides.

Examples of antibiotics include but are not limited to amikacin, gentamicin, kanamycin, neomycin, netilmicin, paromomycin, streptomycin, tobramycin and apramycin, streptovaricins, rifamycins, amoxicillin, ampicillin, azlocillin, carbenicillin, cloxacillin, dicloxacillin, flucloxacillin, mezlocillin, nafcillin, piperacillin, pivampicillin, ticarcillin, cefacetrile, cefadroxil, cefalexin, cefaloglycin cefalotin, cefapirin cefazolin, cephradine, cefaclor, ceforanide, cefotiam cefprozil, cefuroxime, cefdinir, cefditoren, cefixime, cefmenoxime, cefoperazone cefotaxime, cefpiramide, cefpodoxime, ceftazidime, ceftibuten, ceftriaxone, cefepime, cefquinome, doxycycline, sulbactam, tazobactam, clavulanic acid, ampicillin/sulbactam(sultamicillin), co-amoxicillin/clavulanate (or clavulanic acid) and combinations thereof.

Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

In various embodiments, the active pharmaceutical ingredient includes osteoporosis drugs or drugs that will block/modify bone remodeling. Examples of such drugs include, but are not limited to, calcitonin, bisphosphonates, such as for example, alendronate, risedronate, zoledronic acid, ibandronate, etidronate, synthetic hormones for treating osteoporosis, (e.g., teriparatide), Dehydroxymethylepoxyquinomicin (DHMEQ), estrogen receptor agonists/antagonists, such as for example, arzoxifene, genistein, TSE-424, raloxifene, lasofoxifene, basedoxifene. Other drugs such as, for example, MMP inhibitors, such as for example, BB-3364, Ilomastat (GM 6001; Galardin), marimastat, TMI-1 (sulfonamide hydroxamate), neovastat, BAY12-9566, Ro32-3555, SC44463 or combinations thereof. Active pharmaceutical may include HIV-protease inhibitors, such as for example, agenerase, aptivus, crixivan, invirase, kaletra, lexiva, norvir, prezista, reyataz, viracept or a combination thereof. Exemplary active pharmaceutical ingredients include toll-like receptors antagonists, chaperonin 10, superoxide dismutase mimetics, poly(adp)ribose polymerase inhibitors (PARP-1), caspase-1 or interleukin (IL)-1b converting enzyme (ICE) inhibitors, triterpenoids (synthetic or natural), jesterones, cathepsin inhibitors (e.g., OST-4077; Relacitib), dipeptidyl Peptidase IV Inhibitors (DPP-IV), cartilage repair stimulators (e.g., RNI 249, vincaria, reparagen, etc.), leflunomide, boswellic acid, curcumin, withanolides, biolimus, everolimus, zotarolimus, IKK inhibitors, manumycin A, arthritis disease modifying drugs of any sort, including but not limited to calcium fructaborate, anthraquinone derivatives diacerein or rhein, or a combination thereof. Exemplary active pharmaceutical agents also include blockers of nitric oxide synthesis (e.g., L-NAME, L-NMMA, or haloperadol), and blockers of apoptosis (e.g. Aralia cordata or other blockers of p38 MAP-kinase).

Anti-fungal agents can include, but are not limited to, fluconazole, itraconazole, ketoconazole, miconazole, ciclopirox, clotrimazole, econazole, miconazole, nystatin, oxiconazole, terconazole, and tolnaftate.

Anti-protozoal agents can include, but are not limited to, chloroquine, hydroxychloroquine, quinine, primaquine, denzimidazole, piperazine, pyrentel pamoate, praziquantel, ivermectin, diloxanide furoate, metronidazole, eflornithine, furazolidone, idoquinol, paromomycin, emetines, atovaquone, pyrimethamine combined with sulfadiazine, sodium stibogluconate, amphotericin B, nifurtimox, melarsoprol, suramin, and pentamidine.

The at least one pharmaceutical agent of the present invention may be a growth factor. The growth factor may be an osteoinductive and/or cartilage forming protein or molecule that may be used alone or in combination with any of the above agents to stimulate or induce bone or cartilage growth within the joint. Platelet-derived growth factors (PDGFs), bone morphogenetic proteins (BMPs), insulin-like growth factors (IGFs), basic fibroblast growth factor (bFGF), cartilage derived morphogenetic protein (CDMP), and various other bone and cartilage regulatory proteins, such as CD-RAP, are all growth factors that are successful in bone and cartilage regeneration. BMPs and CDMPs, in particular, induce new cartilage and bone formation though a signal cascade that, ultimately, leads to morphogenesis of precursor cells into bone or cartilage cells. CD-RAP is also known in the art to be a regulatory protein synthesized by chondrocytes involved in the formation of type II collagen and, ultimately, cartilage. BMPs, CDMPs, and CD-RAP may be contained within the depot and released from the depot such that the proteins or molecules induce the formation of bone and/or cartilage. Such formation of bone and/or cartilage is useful for the treatment of the degeneration of cartilage and bone associated with osteoarthritis, chondromalacia, rheumatoid arthritis, or any other bone or cartilage degenerative condition.

Examples of such BMPs and CDMPs may include, but are not limited to, BMP-2, BMP-4, BMP-6, BMP-7, BMP-8, and CDMP-1. The BMPs or CDMPs may be available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating BMP from bone are described in U.S. Pat. No. 4,294,753 to Urist and in Urist et al., 81 *PNAS* 371, 1984.

The present application is not limited to the above embodiments of BMPs, CDMPs, and CD-RAP. Rather, any natural or synthetic BMP, CDMP or other osteoinductive or cartilage producing protein or molecule is contemplated by the present invention such as, but not limited to, BMP-1, BMP-2, rhBMP-2, BMP-3, BMP-4, rhBMP-4, BMP-5, BMP-6, rhBMP-6, BMP-7 (also called OP-1), rhBMP-7, BMP-8, BMP-9, BMP-10, BMP-11, BMP-12, BMP-13, BMP-14, BMP-15, BMP-16, BMP-17, BMP-18, GDF-5 (also called CDMP-1), rhGDF-5, and mimetics thereof. Additionally, the present invention may include, separately or in combination with any of the above embodiments, any other protein or molecule that induces bone or cartilage regeneration such as, but not limited to, platelet-derived growth factors (PDGFs), insulin-like growth factors (IGFs), fibroblast growth factor (FGF), LIM mineralization proteins, transforming growth factors (TGF), fibroblast growth factor (FGF), growth differentiation factors (GDF), and mimetics thereof. A more detailed discussion as to how each of these growth factors and/or proteins induce bone and cartilage regeneration may be found in Rengachary, *Neurosurg. Focus,* 13:1-6, 2002;

Reddi, *Arthritis Res*, 3:1-5, 2001; and Varkey et al., *Expert Opin. Drug Deliv.*, 1:19-36, 2004.

In various embodiments, the therapeutic agent comprises botulinum toxin, TGF beta, fibroblast growth factor 18, or a combination thereof.

The depot manufactured in the above example can be administered to a patient using minimally invasive procedures or using a full surgical procedure. Using minimally invasive procedures, such as an arthroscopy, one can make an incision in the skin and muscle of the patient near joint. The endoscope can be pushed through the tissue until it reaches the capsular membrane. An incision can be made in the membrane.

The depot can be rolled or folded or otherwise compressed into a smaller shape. It can be inserted into the proximal opening of the endoscope and pushed until it exits the distal end of the endoscope inside the synovial joint. Once inside the synovial joint, one can unfold, unroll or otherwise uncompress the depot. If the depot has shape memory polymer attached to it, the shape memory polymer may be sufficient to uncompress the depot. If the depot has a lattice similar to an umbrella, one can uncompress the depot by extending the lattice. Alternatively, if one had compressed the depot into a smaller size around an uninflated balloon and placed the depot and the uninflated balloon inside the synovial joint, then one could inflate the balloon, thereby uncompressing the depot. Alternatively, one can use forceps or similar tools to careful unfold, unroll or otherwise uncompress the depot. The use of a tool to open up the depot could occur prior to attachment of some of the depot to the synovial membrane or after attachment of the depot to the synovial membrane at one or more points.

Alternatively, the depot can have a guide wire attached to the depot prior to folding, rolling or compressing the depot. The folded depot and the guide wire can be moved into the synovial joint via the endoscope. Once inside the synovial joint, one can use the guidewire to position the depot to the desired location. The depot can then be attached to the synovial membrane and the guide wire can be used to unroll, unfold, or otherwise uncompress the depot. Alternatively, the guide wire can be used to unroll, unfold, or otherwise uncompress the depot and then position the depot to the desired location for attachment to the synovial membrane.

The depot can be attached to the synovial membrane by any of the attachment devices mentioned above. Sutures, barbs, tacks, staples, tethers, and the like can be passed through the depot and the synovial membrane at various points on the depot to securely attach the depot to the synovial membrane. Some of the adhesive devices can be made from polymers that absorb body fluids and swell, thereby providing an additional mechanism to secure the depot to the synovial membrane. Alternatively, an adhesive can be applied to the surface of the synovial membrane or to the side of the depot which faces the synovial membrane. The surgeon applies pressure to the depot and the synovial membrane until the adhesive cures, thereby securing the depot to the synovial membrane.

In an alternative embodiment, after an incision has been made in the synovial membrane, the physician can replace, wash or flush out the synovial joint by suctioning out the fluids and adding a physiologically neutral solution such as saline, dextrose solution, phosphate buffered saline, Ringer lactate, Sydny's ringers, or Ringer-Locke solution, HT-FRS (BioLife), Synvisc®, Orthovisc®, hyaluronic acids or derivatives thereof or the like. The suctioning of fluids and addition of the physiologically neutral solution can be repeated any number of times for any length of time. The steps can occur simultaneously or as distinctly different steps. Not wishing to be bound to a particular hypothesis, it is believed that the synovial fluid of an inflamed joint contains a myriad of pro-inflammatory cytokines and other pro-inflammatory molecules. Washing, replacing or flushing out the inflamed joint removes most or all of these pro-inflammatory cytokines and other pro-inflammatory molecules and benefits the treatment regimen. Many anti-inflammatory agents, such as antibodies or receptors that specifically bind to pro-inflammatory molecules, exert their action in a sacrificial manner, they are consumed generally stoichiometrically relative to their targets. Thus, removal of the targets of the anti-inflammatory agents from an inflamed synovial joint prior to administration of the pharmaceutical agent provides benefits in such specific binding modes of action as well as with other anti-inflammatory agents.

Washing, flushing or replacing the synovial fluid of the joint with suitable substitutes for synovial fluid of a joint may even help the joint heal faster, thereby lessening the amount of time and the dose of pharmaceutical agents necessary for treatment. After the washing, flushing or replacing the joint fluid, the physician can insert the depot through the endoscope into the joint. In addition, after the joint has been washed, the physician can administer into the joint a dosage of an at least one pharmaceutical agent to help start the treatment, and dosage separate from the pharmaceutical agent which will be released by the depot.

In another embodiment, if one is inserting the depot into a knee, the depot can be placed in the upper lateral gutter of the knee after the depot has been unrolled, unfolded or otherwise uncompressed. Placement of the depot into the upper lateral gutter occurs by inserting the catheter or guidewire during image-guided arthroscopy into the upper compartment of the supra patellar bursa. The compressed or rolled depot is then deployed using SMA springs or an expandable, retractable, frame. After placing the depot in the upper lateral gutter, one secures the depot to the synovial membrane by any of the attachment devices discussed above.

In an alternative embodiment, the physician inserts the endoscope into the patient's body until the distal end is adjacent to the synovial membrane of the joint to be treated. The folded, rolled, compressed depot is inserted into the proximal end of the endoscope and moves through the distal end of the endoscope into the patient's body, adjacent to the synovial membrane. The depot can be unfolded, unrolled, or otherwise uncompressed and placed next to the outside of the synovial membrane. Then the physician can securely attach the depot to the outside of the synovial membrane using any of the attachment devices discussed above. The at least one pharmaceutical agent will dissolve and can pass through the synovial membrane into the synovial joint. One has the option of washing out the synovial fluid even if one attaches the depot to the outside of the synovial membrane.

In another embodiment, an adhesive (listed above) is sprayed onto the synovial membrane in the upper lateral gutter (e.g., supra patellar compartment), using an endoscopic spray device, prior to insertion and deployment of the folded polymer depot onto the surface.

In another embodiment, micro-depot of polymer and drug are sprayed, with the adhesive hydrogel, as a thin layer onto the inner membrane of the synovial bursae using an endoscopic spray device (such as using Micromedics endoscopic fibri-jet spray device).

The depot which has been securely attached to the synovial membrane can be left in place for the pre-determined time. If the depot is not completely biodegradable, one may have to reopen the patient's body to remove the non-resorbable components of the depot.

In an alternative embodiment, the depot containing an internal void is inserted into a joint using the same protocol as described above. Once inside the joint, it is unrolled, unfolded or otherwise uncompressed. Then the at least one pharmaceutical agent is injected into the internal void in the depot using a small gauge needle. The depot is securely attached to the synovial membrane, taking care to keep intact the integrity of the depot walls covering the internal void.

After the depot is securely attached to the synovial membrane, the physician repairs the hole in the synovial membrane, if any, and removes the endoscope, repairing any tissue that was cut during the procedure. The depot releases the at least one pharmaceutical agent over the pre-determined period of time at the pre-determined rate. If the depot is made from resorbable polymers, there may not be a need to remove it from the patient. If the depot is made from non-biodegradable polymers, then the physician may need to remove the depot from the patient using minimally invasive techniques or using open surgical techniques.

Method of Making

In various embodiments, the drug depot comprising the active ingredients can be made by combining a biocompatible polymer and a therapeutically effective amount of the active ingredients or pharmaceutically acceptable salts thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures.

For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic compounds, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as active ingredients, is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this release profile is not desired.

In various embodiments, the drug depot can be prepared by mixing or spraying the drug with the polymer and then molding the depot to the desired shape (with or without anchoring members).

The drug depot may also be prepared by combining a biocompatible polymer and a therapeutically effective amount of at least one analgesic agent or anti-inflammatory agent and forming the implantable drug depot from the combination.

The thermoplastic polymer, in various embodiments, may be applied to the frame of the depot (e.g, nitinol, memory shape alloy, etc.) or the frame can be included in a mold and the thermoplastic polymer can be applied thereto.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating a tissue within a synovial joint in a patient in need of such treatment, the method comprising inserting a drug depot through the synovial joint and attaching the drug depot to the inside of the synovial joint capsule so that the drug depot does not substantially interfere with movement of the joint, wherein said depot extends along a longitudinal axis and comprises a polymer, at least one pharmaceutical agent, one or more first barbs slanting backwards along the longitudinal axis and one or more second barbs slanting forwards along the longitudinal axis; wherein the one or more first barbs and the one or more second barbs comprise a shape memory polymer and a frame that can fold and unfold, and the one or more first barbs and the one or more second barbs are inflatable and configured to be filled with air or fluid to expand the one or more first barbs and the one or more second barbs and inflating the one or more first barbs and the one or more second barbs by filling them with air or fluid.

2. A method according to claim 1, wherein the drug depot further comprises a chamber for holding at least one pharmaceutical agent and the pharmaceutical agent is released from the chamber.

3. A method according to claim 1, wherein the drug depot is attached to tissue comprising the upper lateral gutter, pre-patellar bursa, infra-patellar fat pad, infra-patellar bursa and/or synovial membrane of a knee.

4. A method according to claim 1, further comprising washing or flushing the joint with a physiological neutral solution to remove pro-inflammatory cytokines prior to inserting the depot into the synovial joint.

5. A method according to claim 1, wherein the at least one pharmaceutical agent comprises one or more anti-inflammatory agents, antibiotics, antiviral agents, anti-protozoa agents, anti-fungal agents, anti-parasitic agents, analgesics, growth factors, cytokines, lubricants, and/or nutrients.

6. A method according to claim 1, further comprising compressing the drug depot prior to inserting the drug depot and uncompressing the drug depot after inserting the drug depot through the synovial membrane.

7. A method according to claim 1, wherein the at least one pharmaceutical agent is released from the drug depot over a period of at least 6 months.

8. An implantable drug depot useful for treating tissue within a synovial joint in a patient in need of such treatment, the implantable drug depot extending along a longitudinal axis and comprising a therapeutically effective amount of a pharmaceutical agent and a polymer, the depot capable of being attached to an inside of a synovial joint capsule so that the drug depot does not substantially interfere with movement of the joint and the drug depot is capable of releasing the pharmaceutical agent over a period of at least three days and the drug depot comprises one or more first barbs slanting backwards along the longitudinal axis and one or more second barbs slanting forwards along the longitudinal axis; wherein the one more first barbs and the one or more second barbs comprise a shape memory polymer and a frame that can fold and unfold to attach to the inside of the joint capsule, and the one or more first barbs and the one or more second barbs are inflatable and configured to be filled with air or fluid to expand the one or more first barbs and the one or more second barbs.

9. An implantable drug depot according to claim 8, wherein the drug depot is attached to tissue comprising the upper lateral gutter, prepatellar bursa, infra-patellar fat pad, infra-patellar bursa and/or synovial membrane of a knee.

10. An implantable drug depot according to claim 8, wherein the one or more first barbs and the one or more second barbs swell when they come in contact with a fluid.

11. An implantable drug depot according to claim 8, drug depot further comprises a chamber for holding at least one pharmaceutical agent and the pharmaceutical agent is released from the chamber.

12. A method of reducing pain and/or inflammation of tissue within a synovial joint in a patient in need of such treatment, the method comprising inserting a drug depot through the synovial joint and attaching the drug depot to the inside of the synovial joint capsule so that the drug depot allows normal articulation of the synovial joint and does not substantially interfere with movement of the joint, wherein the depot extends along a longitudinal axis and comprises a shape memory polymer in one or more first barbs slanting backwards along the longitudinal axis, one or more second barbs slanting forwards along the longitudinal axis and at least one analgesic and/or anti-inflammatory agent and the drug depot is capable of releasing the at least one analgesic and/or anti-inflammatory agent over a period of at least three days, wherein the drug depot is inserted into the patient in a rolled, folded or compressed state and is unrolled, unfolded or uncompressed after the drug depot is inserted into the patient, and the one or more first barbs and the one or more second barbs are inflatable and configured to be filled with air or fluid to expand the one or more first barbs and the one or more second barbs and inflating the one or more first barbs and the one or more second barbs by filling them with air or fluid.

13. An implantable drug depot useful for treating tissue within a synovial joint in a patient in need of such treatment, the implantable drug depot extending along a longitudinal axis and comprising a therapeutically effective amount of a pharmaceutical agent and a polymer, the depot comprising one or more first barbs slanting backwards along the longitudinal axis and one or more second barbs slanting forwards along the longitudinal axis comprising a shape memory polymer capable of being attached to an inside of a synovial joint capsule so that the drug depot does net substantially interfere with movement of the joint and the drug depot is capable of releasing the pharmaceutical agent over a period of at least three days, wherein the one or more first barbs and the one or more second barbs (i) swell when it they comes in contact with a bodily fluid (ii) and comprise a frame that folds, compresses, or rolls in a first state and unfolds, uncompresses, or unrolls in a second state after the drug depot is inserted into the inside of the synovial joint, and the one or more first barbs and the one or more second barbs are inflatable and configured to be filled with air or fluid to expand the one or more first barbs and the one or more second barbs.

14. An implantable drug depot according to claim 8, wherein the at least one pharmaceutical agent comprises clonidine.

15. An implantable drug depot according to claim 13, wherein the at least one pharmaceutical agent comprises clonidine.

16. A method according to claim 12, wherein the at least one pharmaceutical agent comprises clonidine.

17. A method according to claim 1, wherein the depot comprises at least two first barbs and at least two second barbs.

18. A method according to claim 1, wherein the fluid comprises dextrose, saline, Ringers Lactate, and combinations thereof.

19. A method according to claim 1, wherein each of the one or more first barbs and each of the one or more second barbs comprises a tube disposed therein that once inflated will fill the barb causing it to expand.

20. A method according to claim 19, wherein only a portion of the one or more first barbs and only a portion of the one or more second barbs are inflatable.

* * * * *